(12) United States Patent
Perov et al.

(10) Patent No.: US 7,598,037 B2
(45) Date of Patent: Oct. 6, 2009

(54) METHOD FOR IMPLEMENTING NON-DESTRUCTIVE QUALITY CONTROL OF SUBSTRATES AND PRINTED BIOLOGICAL MICROARRAYS

(75) Inventors: Alexander N. Perov, Woodridge, IL (US); Darrell P. Chandler, Yorkville, IL (US)

(73) Assignee: U Chicago Argonne, LLC, Chicago, IL (US)

( * ) Notice: Subject to any disclaimer, the term of this patent is extended or adjusted under 35 U.S.C. 154(b) by 334 days.

(21) Appl. No.: 11/485,203

(22) Filed: Jul. 12, 2006

(65) Prior Publication Data

US 2007/0072213 A1    Mar. 29, 2007

Related U.S. Application Data

(60) Provisional application No. 60/721,041, filed on Sep. 27, 2005.

(51) Int. Cl.
*C12Q 1/68* (2006.01)
*C12M 1/00* (2006.01)
*G01N 15/06* (2006.01)

(52) U.S. Cl. .................. 435/6; 435/283.1; 435/287.2; 435/288.7; 422/68.1; 422/82.05

(58) Field of Classification Search .......... None
See application file for complete search history.

(56) References Cited

U.S. PATENT DOCUMENTS

| | | | | |
|---|---|---|---|---|
| 2002/0095073 | A1* | 7/2002 | Jacobs et al. | 600/300 |
| 2004/0063098 | A1* | 4/2004 | Hargreaves | 435/6 |
| 2005/0227358 | A1* | 10/2005 | McEntee et al. | 436/5 |

OTHER PUBLICATIONS

Taylor et al "Impact of surface chemistry and blocking stratagies on DNA microarrays" Nucleic Acids Research, 2004, vol. 31, No. 16e87.*

* cited by examiner

*Primary Examiner*—B J Forman
(74) *Attorney, Agent, or Firm*—Joan Pennington

(57) ABSTRACT

A method and apparatus are provided for implementing non-destructive quality control of substrates and printed biological microarrays. A method and apparatus are provided for implementing quality control of gel-based microarrays prepared by dispensing a gel-forming composition on a solid substrate. The method utilizes the difference between the wettability properties of a supporting substrate and a gel, where the gel is hydrophilic. Condensation of vapor of a chemically inert water-soluble liquid, such as water or glycerol, on the surface of a substrate under inspection creates a layer of tiny droplets that affect both transmission and scattering of light on the surface. A pattern of condensation, characterized by spatial distribution, average size of the droplets and spacing between the droplets, reflects variation in wetting properties of the substrate. The pattern of condensation circumscribes printed microarray features to be non-destructively imaged and analyzed.

16 Claims, 3 Drawing Sheets

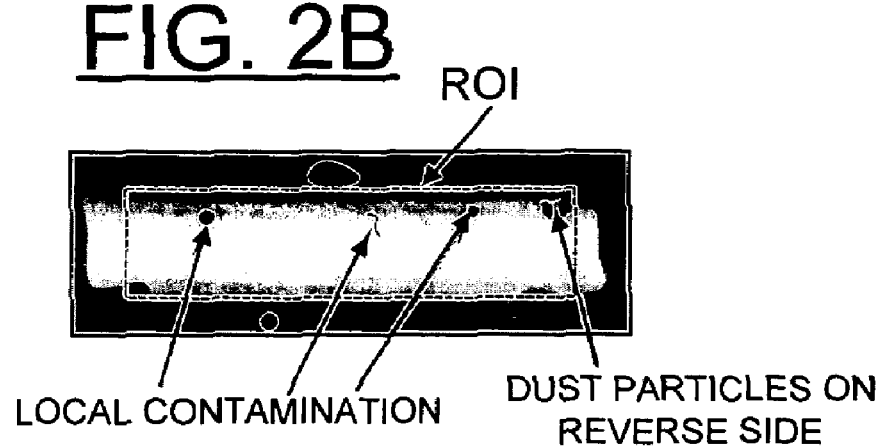
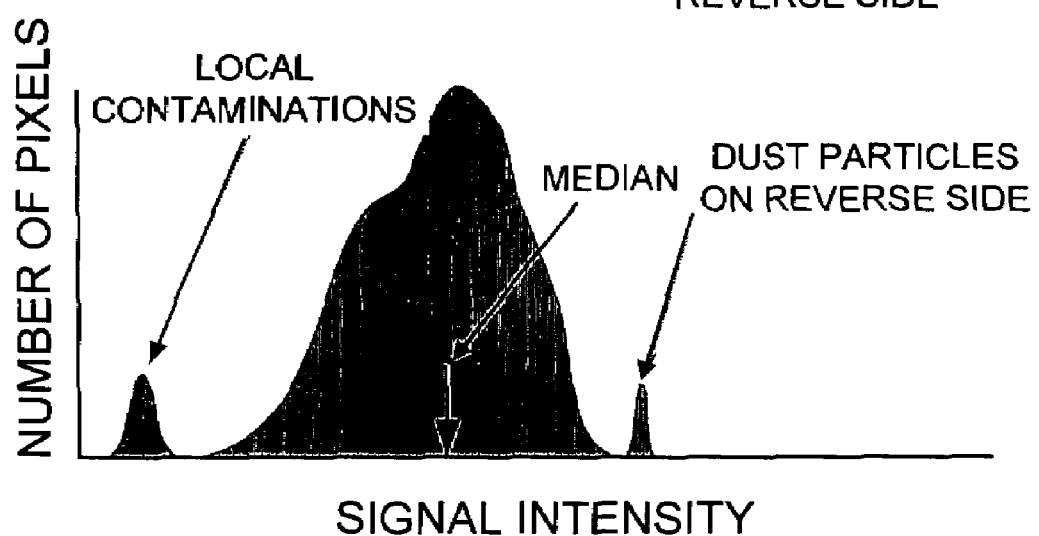

METHOD FOR IMPLEMENTING NON-DESTRUCTIVE QUALITY CONTROL OF SUBSTRATES AND PRINTED BIOLOGICAL MICROARRAYS

This application claims the benefit of U.S. Provisional Application No. 60/721,041, filed on Sep. 27, 2005.

CONTRACTUAL ORIGIN OF THE INVENTION

The United States Government has rights in this invention pursuant to Contract No. W-31-109-ENG-38 between the United States Government and Argonne National Laboratory.

FIELD OF THE INVENTION

The present invention relates to a method and apparatus for the quality control of printed microarrays. More specifically, this invention relates to a method and apparatus for implementing non-destructive quality control of solid substrates for biological microarrays; and a method and apparatus for implementing quality control of microarrays fabricated by contact or non-contact deposition techniques. A preferred embodiment of the invention pertains to quality control of gel-element microarrays, typically prepared by dispensing a gel-forming composition on a solid substrate, such as glass or plastic surfaces.

DESCRIPTION OF THE RELATED ART

Variations in substrate quality, for example, chemical or physical non-uniformities, substantially affect the quality of microarrays during the printing process, significantly decrease the yield of useable microarrays from any one manufacturing lot, and cause substantial variability in their bio-analytical characteristics and response or irreproducibility of their analytical characteristics. Likewise, variations in microarray feature quality, for example, spot morphology or probe density, substantially affect microarray bio-analytical characteristics and response or irreproducibility of their analytical characteristics.

A rapid and non-destructive method and decision criteria for substrate and microarray feature quality control and quality assurance is therefore required in order to improve overall manufacturing process control, and subsequent reproducibility and performance of microarrays.

Known methods of substrate characterization rely either on sophisticated equipment such as atomic force microscope or infrared Fourier spectrometers, or test printing on certain selected slides. None of these techniques are rapid, reliable, or non-destructive. Known methods for characterizing microarray features on printed microarrays include staining with fluorescent dyes, or functional tests of selected microarrays from individual batches. In either case, the present methods do not allow non-destructive, quantitative, thorough inspection of each and every substrate and each and every microarray, which is the preferred solution for production scale-up and successful commercialization of microarray-based diagnostic tests.

In order to illustrate the present invention, we describe methods and techniques for quality control and quality assurance of gel-element microarrays, manufactured via co-polymerization chemistry and conventional contact printing robotics on either glass or plastic substrates. A preferred embodiment for performing substrate and microarray inspection is an optical system that can detect and quantify missing, deformed or misplaced array elements as well as particles of dirt or other contamination on the microarray substrate. For those skilled in the art and in the spirit of the invention, however, it is understood that the invention is broadly applicable to many types of printed microarrays and substrates.

Typical gel compositions used to form the elements of a gel-element microarray are transparent, colorless, rather thin (<10 micron), and have a refractive index that does not differ much from that of glass or plastic. For this reason, gel-element features are very difficult to visualize other than by staining them with some dye, a procedure that usually leaves the microarray contaminated and unsuitable for subsequent diagnostic tests or biological analyses.

Important objects of the present invention are to provide a method and apparatus for implementing non-destructive quality control of substrates for biological microarrays.

Important objects of the present invention are to provide a method and apparatus for implementing quality control of microarray features deposited by contact and non-contact printing methods.

Important objects of the present invention are to provide a method and apparatus for implementing quality control of gel-based microarrays prepared by dispensing a gel-forming composition on a solid substrate.

Other important aspects of the present invention are to provide such method and apparatus for implementing non-destructive quality control of substrates for biological microarrays; such method and apparatus for implementing quality control of microarray features deposited by contact and non-contact printing methods; and such method and apparatus for implementing quality control of gel-based microarrays prepared by contract dispensing a gel-forming composition on a solid substrate; each substantially without negative effect and that overcome some of the disadvantages of prior art arrangements.

SUMMARY OF THE INVENTION

In brief, a method and apparatus are provided for implementing non-destructive quality control of substrates and for implementing non-destructive quality control of printed microarrays. Condensation of vapor of a chemically inert water-soluble liquid, such as water vapor or another chemically neutral and relatively volatile liquid, such as glycerol, on the surface of a substrate under inspection creates a layer of tiny droplets that affect both transmission and scattering of light on the surface. A pattern of condensation, characterized by spatial distribution, average size of the droplets and spacing between the droplets, is used to identify variation in wetting properties of the substrate.

The method of the invention enables the detection, visually or by machine, of areas of a specific type of vapor condensation on the printed microarray, which indicates the presence of undesirable variations of wettability and/or substrate contaminations, and circumscribes microarray features to be inspected for presence and absence, morphology, pitch regularity, and other geometrical and quantifiable attributes.

In accordance with features of the invention, in more hydrophobic regions the droplets are smaller and more densely spaced, so these regions are brighter in reflected light and less transparent in transmitted light. These variations in brightness and transparency are distinct and are easily observed and analyzed directly by the operator or by means of an automated machine vision system. The test is non-destructive as the condensate readily evaporates and leaves both the substrate and microarray features uncontaminated.

A method and apparatus are provided for implementing quality control of microarrays prepared by dispensing a gel-forming composition on a solid substrate. The method utilizes the difference between wettability properties of the solid substrate and a gel, where the gel is hydrophilic. Condensation of water vapor on a solid substrate surface results in formation of multiple densely spaced small droplets on the surface between the array elements while the array elements remain clear. Since the droplets reduce transmittance of the substrate due to light scattering, the array becomes visible in both transmitted and reflected light. Evaluation of the array quality is performed visually by the operator using a microscope or with an automated machine vision system. Since the condensate evaporates without any residue, the test is non-destructive.

In accordance with features of the invention, the method of the invention enables automating the quality control of microarray substrates and printed microarrays, enabling decision making of acceptance or rejection of substrates and completely fabricated microarrays based on analysis of the digital image of a condensation pattern.

BRIEF DESCRIPTION OF THE DRAWINGS

The present invention together with the above and other objects and advantages may best be understood from the following detailed description of the preferred embodiments of the invention illustrated in the drawings, wherein:

FIGS. 2A and 2B respectively are a substrate image histogram with signal intensity shown along a horizontal axis and number of pixels shown along a vertical axis, and a display of a region of interest (ROI) together illustrating defects of microarray substrates and characteristic features of the substrate image histogram associated with the defects detected with the apparatus of FIG. 1 in accordance with the preferred embodiment.

DETAILED DESCRIPTION OF THE PREFERRED EMBODIMENTS

Figure 1:
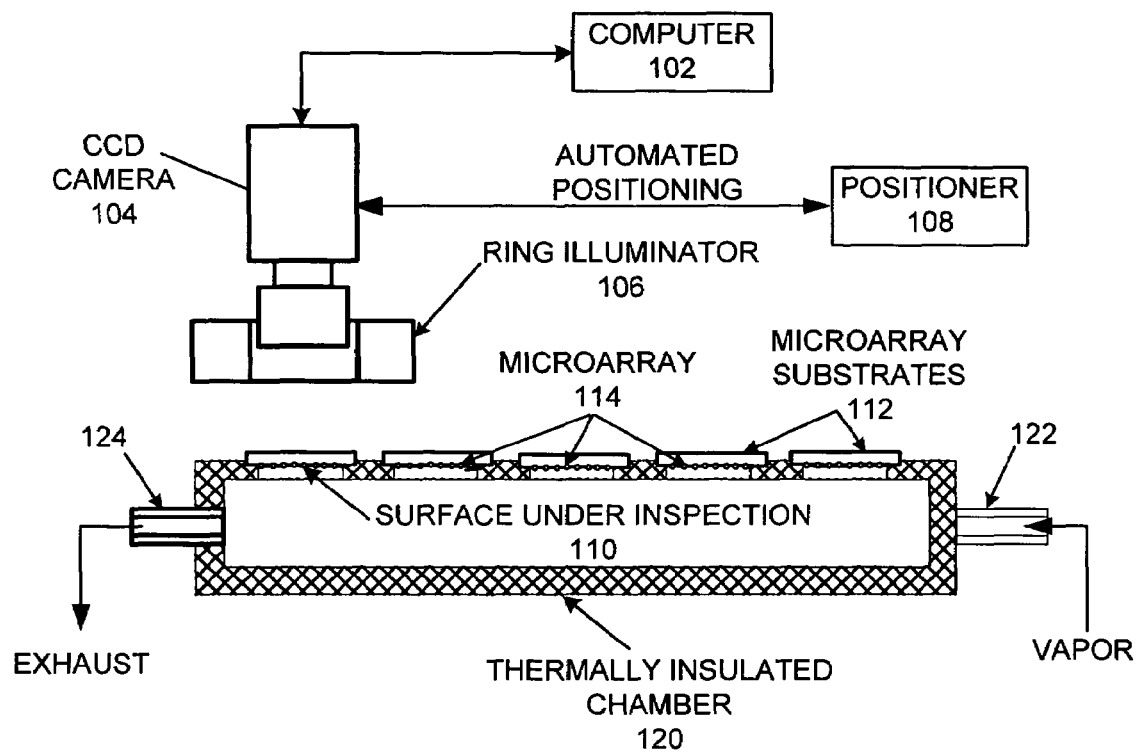
FIG. 1 is a schematic and block diagram representation illustrating apparatus for implementing methods for non-destructive quality control of substrates for biological microarrays; for implementing methods for quality control of microarray features deposited by contact and non-contact printing; and for implementing methods for quality control of gel-based microarrays prepared by contract printing of a gel-forming composition on a glass or plastic substrate in accordance with the preferred embodiment.

As used in the following description and claims, the following definitions apply:

A biological microarray is defined herein as an array of biomolecular probes immobilized at spatially ordered locations on a solid substrate.

A biomolecular probe is defined as a synthetic or natural compound capable of specific interaction with biological molecules such as DNA, RNA, or protein.

Biomolecular probes may be delivered to the immobilization sites on the substrate by any known dispensing technique, either contact or non-contact.

The process of dispensing probes onto a substrate is defined as a printing method. Accordingly, microarrays fabricated by printing are referred to as printed microarrays, as opposed to microarrays fabricated by synthesizing the probes on the substrate, in situ. In the process of printing, the probes are typically dispensed on the substrates as one component of an aqueous solution.

In the preferred embodiment, the printing solution is a gel-forming composition, which, upon gel polymerization, considerably enhances the immobilization capacity of the substrate by creating a highly porous three-dimensional polymer structure directly on each immobilization site. Microarrays fabricated in this manner are referred to as gel-element or gel-based microarrays.

The material immobilized onto discrete sites on the substrate during microarray manufacture is defined as a microarray feature, which is in contradistinction to the surrounding surface of the substrate.

To allow high-density printing and improve feature morphology, the wettability of microarray substrates is typically adjusted to prepare a moderately hydrophobic surface, where the preferred contact angle for the printed solution is in the range of 40 to 80 degrees. The surface chemistry of the substrate is typically modified to provide conditions for either direct immobilization of the probes onto the substrate surface; or to immobilize discrete gel-elements onto the substrate surface. Optically, microarray substrates are preferably transparent, black or reflective. In each case, the substrate surface is normally polished to minimize undesirable light scattering.

Microarray substrates can consist of glass, for example a standard microscope slide, plastics or other materials, such as silicon or sapphire.

While the following detailed description generally refers to the condensation of water vapor, the present invention is not limited to the condensation of water vapor, it should be understood that a chemically inert water-soluble liquid, or chemically neutral and relatively volatile liquid, such as glycerol, could be used to implement methods of the invention. Likewise, it should be understood that the present invention is not limited to gel-element microarrays; it should be understood that various array surfaces and printed microarrays could be analyzed and assessed in accordance with the methods of the invention.

In accordance with features of the preferred embodiments, methods are provided for implementing non-destructive quality control of substrates and microarray features for biological microarrays. Condensation of water vapor on the surface of a substrate under inspection is provided to create a layer of tiny droplets that affect both transmission and scattering of light on that surface. The pattern of condensation, characterized by spatial distribution of average size of the droplets and spacing between them, reflects variations of wetting properties of the substrate: in more hydrophobic regions, the droplets are smaller and spaced more densely, so these regions are brighter in reflected light and less transparent in transmitted light. These variations of brightness and transparency are distinct and can be easily observed and analyzed either directly, by the operator, or by an automated machine vision or imaging system. The test is non-destructive as the condensate readily evaporates leaving the microarray uncontaminated.

The gel that forms the elements of gel-element arrays is transparent, colorless, thin, such as less than 10 micron, and has a refractive index that does not differ much from that of glass or plastic. For this reason, gel-based arrays are very difficult to visualize. Staining the gel-based arrays with some dye that could render them visible typically causes irreversible contamination of the array.

In accordance with features of the preferred embodiments, a quality-control method for mass production of gel-based microarrays manufactured by contact printing of gel-forming composition on glass or plastic substrates is provided that can detect missing, deformed or misplaced array elements as well as dust particles and other possible contaminations on the microarray substrate. In contrast to the gel-supporting surface, gel-elements are hydrophilic. Condensation of water vapor on the microarray results in formation of multiple densely spaced small droplets on the substrate surface between the array elements while the array elements remain clear. Since the droplets substantially reduce transmittance of the substrate due to increased light scattering, the microarray elements become distinctly visible and circumscribed in both transmitted and reflected light. Evaluation of the microarray quality can be performed either visually by the operator using a microscope or by means of an automated machine vision system. The test is non-destructive as the water vapor condensate evaporates without any residue.

Having reference now to the drawings, in FIG. 1 there is shown an exemplary automated quality control apparatus generally designated by the reference character 100 for implementing non-destructive quality control of substrates for biological microarrays and implementing non-destructive quality control for mass production of gel-based microarrays in accordance with the preferred embodiment.

Automated quality control apparatus 100 includes a computer 102 coupled to a detector such as a charge coupled device (CCD) camera 104. Automated quality control apparatus 100 includes a ring illuminator 106 and a positioner 108 provided with the CCD camera 104, for example, for sequentially illuminating a surface 110 of one substrate 112 under test. As shown in FIG. 1, each of the plurality of substrates 112 carries a respective pattern of printed microarray elements 114.

It should be understood that substrates 112 without microarray elements 114 advantageously are processed using the automated quality control apparatus 100 for implementing non-destructive quality control of substrates Automated quality control apparatus 100 includes a thermally insulated chamber 120 that receives the plurality of substrates 112 carrying the respective microarray elements 114 with the surface 110 under test of each of the plurality of substrates 112 disposed within the chamber. A source of moist warm air, for example, having a temperature greater than room temperature, and the moist air having a dew point higher than the temperature of the substrate, is applied to an input port 122 of the thermally insulated chamber 120. A carrier gas at the input port 122 of the thermally insulated chamber 120, such as air, nitrogen, argon, or the like, transports a liquid in vapor phase, such as water vapor, glycerol vapor, or other liquid vapor. The thermally insulated chamber 120 includes an exhaust port 124 located at an opposite end from the input port 122. Condensation of water vapor is provided on the surface 110 of the substrate 112 under inspection to create a layer of tiny droplets that affect both transmission and scattering of light on that surface.

FIGS. 2A and 2B together illustrate exemplary defects of microarray substrates and characteristic features of the substrate image histogram associated with the defects detected with the apparatus 100. In FIGS. 2A and 2B, local contaminations and dust particles on a reverse side are illustrated. In the histogram of FIG. 2A, an arrow indicates a median.

Figure 3:
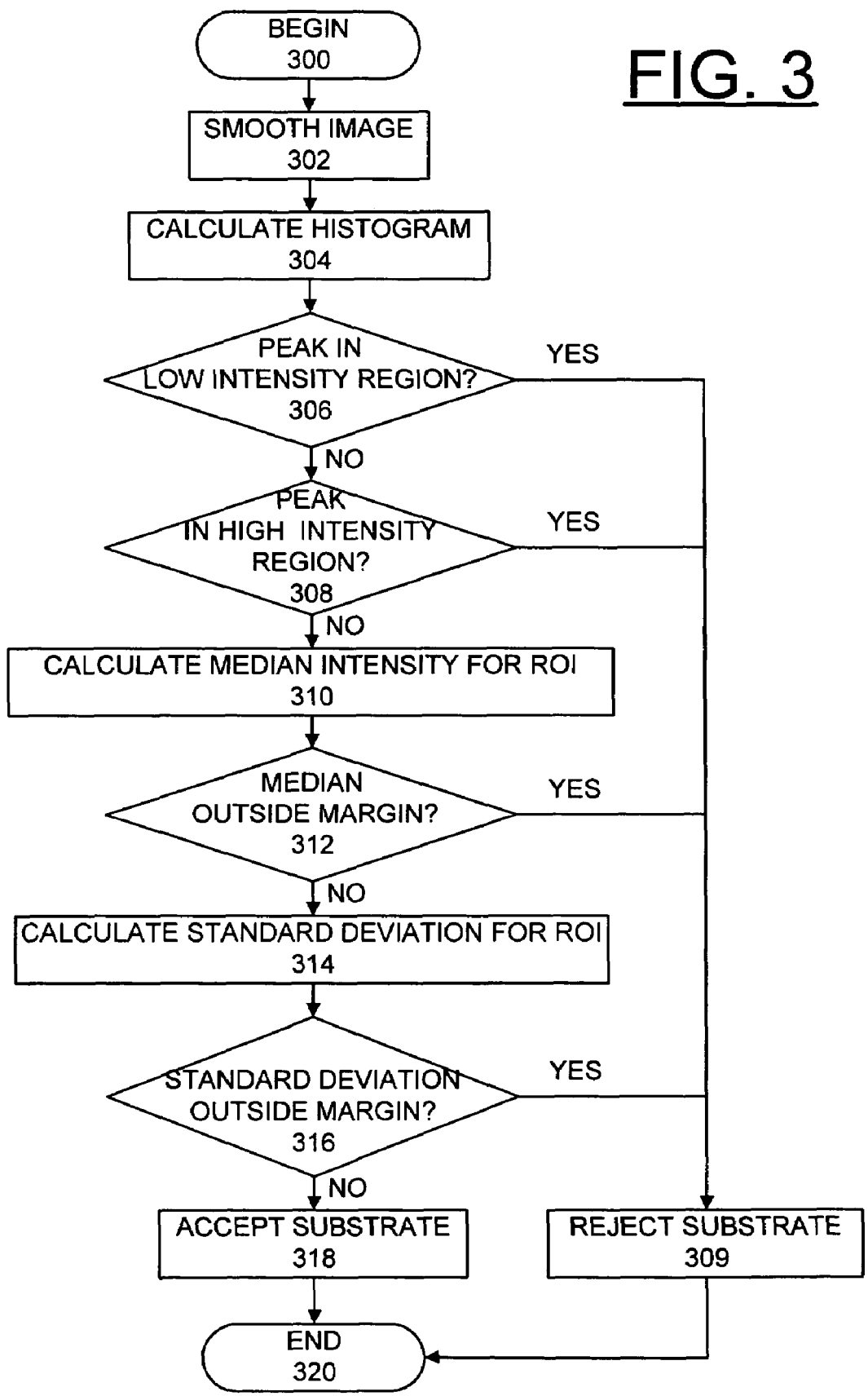
FIG. 3 is a flow chart illustrating exemplary steps for implementing methods for non-destructive quality control of substrates for biological microarrays in accordance with the preferred embodiment.

In accordance with features of the preferred embodiments of the invention, automated quality control of substrates, such as illustrated in the exemplary steps of the flow chart of FIG. 3, advantageously is based on the following practical considerations:

Features of the substrate surface 110 that may affect sample transfer from the pin to the substrate and/or cause subsequent droplet migration are those with a characteristic linear scale comparable to or exceeding the mean droplet diameter used to form microarray features 114.

The largest droplets of the water vapor condensate are typically at least ten times smaller than the droplets of microarray elements 114.

Defects of the substrate working surface 110 can be classified into one of the following three categories: (1) relatively smooth variations of wettability due to inhomogeneous chemical activation; (2) localized spots of abnormally high wettability due to accidental chemical contamination; (3) particulate contaminations which are typically hydrophilic. In a condensation pattern recorded in reflected light, the latter two categories (2) and (3) give characteristic distinct dark spots.

Particulate contaminations on the reverse side of the substrate 112 should generally be considered as a reason for substrate rejection because they may readily be transferred to the working surfaces 110 in the process of substrate handling. In contrast to the particles on the working surface 110, those located on the reverse side of the substrate are bright in reflected light.

Referring now to FIG. 3, there are shown exemplary steps for implementing methods for non-destructive quality control of substrates for biological microarrays in accordance with the preferred embodiment starting with image processing at a block 300. First the image is smoothed using an appropriate imaging analysis technique such as a numerical filtering algorithm for calculating a moving average as indicated in a block 302. The purpose of filtering is to eliminate small-scale signal variations caused by light scattering on individual droplets of the condensate. Then the computer generates a histogram of the image as indicated in a block 304 and analyzes the image histogram to identify characteristic features associated with localized contaminations and dust particles, such as shown in FIG. 2.

Checking for a peak signal in a low intensity region and a high intensity region is performed as indicated in respective decision blocks 306 and 308. The substrate is rejected if a peak signal is identified in the low intensity region or the high intensity region as indicated in a block 309. If the substrate has not been rejected based on histogram analysis at decision blocks 306 and 308, its average wettability and spatial variations of the wetting properties are evaluated, for example, by calculating a median intensity as indicated in a block 310 and by calculating a standard deviation of the signal, as indicated in a block 314, respectively. At blocks 310 and 314, the calculations may be restricted to the Region of Interest (ROI) defined as a region on a substrate 112 designated for array printing. The calculated median and standard deviations are compared to predetermined tolerance margins as indicated in respective decision blocks 312 and 316. The substrate is accepted as indicated in a block 318 if both the median signal intensity and the standard deviation fall within tolerance margins that are assumed to be determined experimentally. The image processing is completed as indicated in a block 320.

Having reference again to FIG. 3, those skilled in the art will understand that various different pattern recognition techniques can be applied to a digital microarray image to extract information and create decision logic for quality control and quality assurance of printed microarrays.

While the present invention has been described with reference to the details of the embodiments of the invention shown in the drawing, these details are not intended to limit the scope of the invention as claimed in the appended claims.

What is claimed is:

1. A method for implementing non-destructive quality control of substrates for receiving microarray features of biological microarrays in an automated machine vision system, said method comprising the steps of:

creating a layer of condensate droplets of a chemically inert water-soluble liquid on a surface of a substrate under inspection; said condensate droplets being densely spaced droplets having an average size substantially less than the microarray features; said layer of condensate droplets affecting both transmission and scattering of light on the surface; said layer of said condensate droplets of said chemically inert water-soluble liquid evaporating without any residue;

illuminating said surface of said substrate under inspection;

detecting an image of said illuminated surface of said substrate under inspection; and identifying a pattern of condensate droplets from said detected image of said surface of said substrate under inspection, said pattern characterized by spatial distribution, average size of the droplets and spacing between the droplets, reflecting variation in wetting properties of the substrate; and utilizing said identified pattern with the automated machine vision system for visually detecting an area indicating presence of undesirable variation of wettability and rejecting said substrate under inspection, responsive to detecting the area indicating presence of undesirable variation of wettability.

2. A method for implementing non-destructive quality control of substrates for biological microarrays as recited in claim 1 wherein the step of creating a layer of condensate droplets includes using water for said chemically inert water-soluble liquid.

3. A method for implementing non-destructive quality control of substrates for biological microarrays as recited in claim 1 wherein the step of creating a layer of condensate droplets includes using glycerol for said chemically inert water-soluble liquid.

4. A method for implementing non-destructive quality control of substrates for biological microarrays as recited in claim 1 wherein said chemically inert water-soluble liquid is in a vapor phase and wherein the steps of creating a layer of condensate droplets includes providing said surface of said substrate under inspection within a thermally insulated chamber, and flowing carrier gas through said chamber, said carrier gas transporting said chemically inert water-soluble liquid in vapor phase.

5. A method for implementing non-destructive quality control of substrates for biological microarrays as recited in claim 4 wherein the step of flowing carrier gas through said chamber includes using a selected one of air or nitrogen for said carrier gas.

6. A method for implementing non-destructive quality control of substrates for biological microarrays as recited in claim 1 wherein the steps of identifying a pattern of condensate droplets on said surface of said substrate under inspection includes illuminating said surface of said substrate under inspection, collecting a digital image, and filtering said digital image.

7. A method for implementing non-destructive quality control of substrates for biological microarrays as recited in claim 6 further includes performing digital analysis of said digital image.

8. A method for implementing non-destructive quality control of substrates for biological microarrays as recited in claim 7 further includes calculating statistical characteristics and metrics for at least a portion of said digital image to identify characteristic features associated with non-uniform wettability, localized contaminations and dust particles.

9. A method for implementing non-destructive quality control of substrates for biological microarrays as recited in claim 8 further includes rejecting said substrate responsive to said calculated characteristics and metrics being outside predefined upper and lower tolerance margins; and further includes experimentally determining said predefined upper and lower tolerance margins.

10. A method for implementing non-destructive quality control of substrates for biological microarrays as recited in claim 8 further includes calculating a histogram for said digital image; and calculating a standard deviation for at least a portion of said histogram for said digital image.

11. A method for implementing non-destructive quality control of printed biological microarrays in an automated machine vision system, said method comprising the steps of:

creating a layer of condensate droplets of a chemically inert water-soluble liquid on a surface of a microarray under inspection; said condensate droplets being densely spaced droplets having an average size of at least ten times smaller than microarray features said layer of condensate droplets affecting both transmission and scattering of light on the surface; said layer of said condensate droplets of said chemically inert water-soluble liquid evaporating without any residue;

illuminating said surface of said microarray under inspection;

detecting an image of said illuminated surface of said microarray under inspection; and identifying a pattern of condensate droplets from said detected image of said surface of said microarray under inspection, said pattern characterized by spatial distribution, average size of the droplets and spacing between the droplets, reflecting variation in wetting properties of said surface of said microarray; and utilizing said identified pattern with the automated machine vision system for visually detecting a presence of undesirable variation of microarray features; and rejecting said microarray under inspection responsive to visually detecting the presence of undesirable variation of microarray features.

12. A method for implementing non-destructive quality control of printed biological microarrays as recited in claim 11 wherein said chemically inert water-soluble liquid includes a selective one of water and glycerol.

13. A method for implementing non-destructive quality control of printed biological microarrays as recited in claim 11 wherein said chemically inert water-soluble liquid is in a vapor phase and wherein the steps of creating a layer of condensate droplets includes providing said surface of said substrate under inspection within a thermally insulated chamber, and flowing carrier gas through said chamber, said carrier gas transporting said chemically inert water-soluble liquid in vapor phase; said carrier gas including a selected one of air or nitrogen.

14. A method for implementing non-destructive quality control of printed biological microarrays as recited in claim 11 wherein the step of identifying a pattern of condensate droplets on said surface of said microarray under inspection further includes the steps of collecting and processing said image to circumscribe said microarray features to be inspected for presence of said microarray features, morphology of said microarray features, pitch of said microarray features, and regularity of said microarray features.

15. A method for implementing non-destructive quality control of printed biological microarrays as recited in claim 14 further includes processing said image to circumscribe microarray features to be inspected for predefined quantifiable attributes of said microarray features.

16. A method for implementing non-destructive quality control of printed biological microarrays as recited in claim 11 wherein said microarrays are gel-based microarrays.

\* \* \* \* \*